US006855263B2

United States Patent
Trese et al.

(10) Patent No.: US 6,855,263 B2
(45) Date of Patent: Feb. 15, 2005

(54) RAPID PROCESS FOR PURIFICATION AND CONCENTRATION OF PLASMIN

(75) Inventors: Michael T. Trese, Bloomfield Hills, MI (US); George A. Williams, Grosse Pointe Park, MI (US); Michael K. Hartzer, Rochester Hills, MI (US); Wendelin A. Dailey, Orion, MI (US); Craig J. Bell, E. Swanzey, NH (US)

(73) Assignee: Nuvue Technologies, Inc., Keene, NH (US)

( * ) Notice: Subject to any disclaimer, the term of this patent is extended or adjusted under 35 U.S.C. 154(b) by 143 days.

(21) Appl. No.: 10/201,125

(22) Filed: Jul. 23, 2002

(65) Prior Publication Data

US 2004/0024344 A1 Feb. 5, 2004

(51) Int. Cl.[7] .................. B01D 15/08; G01N 30/00; G01N 30/02; G01N 30/04
(52) U.S. Cl. .................. 210/806; 210/656; 210/660; 210/669; 210/690; 435/2; 435/217; 436/177; 436/523; 436/524; 530/412; 530/413; 530/417
(58) Field of Search .................. 210/656, 660, 210/669, 690, 749, 767, 782, 806; 435/2, 176, 216, 217; 436/177, 178, 523, 524, 528; 502/405; 530/412, 413, 415, 416, 417, 427, 811, 830; 422/44

(56) References Cited

U.S. PATENT DOCUMENTS

| | | | | |
|---|---|---|---|---|
| 3,943,245 A | * | 3/1976 | Silverstein | 530/380 |
| 4,198,335 A | * | 4/1980 | Collen | 530/392 |
| 4,328,314 A | * | 5/1982 | Horiguchi et al. | 435/212 |
| 4,356,958 A | * | 11/1982 | Kolobow et al. | 494/43 |
| 4,604,358 A | * | 8/1986 | Fisher et al. | 435/217 |
| 4,724,207 A | * | 2/1988 | Hou et al. | 435/180 |
| 4,774,087 A | * | 9/1988 | Wu et al. | 424/94.64 |
| 5,064,942 A | * | 11/1991 | Duhl Clemmensen et al. | 435/7.21 |
| 5,134,065 A | * | 7/1992 | Sanzo et al. | 435/70.3 |
| 5,252,216 A | * | 10/1993 | Folena-Wasserman et al. | 210/635 |
| 5,371,007 A | * | 12/1994 | Linnau et al. | 435/217 |
| 5,556,766 A | * | 9/1996 | Linnau et al. | 435/68.1 |
| 6,183,692 B1 | * | 2/2001 | Trese et al. | 422/61 |
| 6,207,066 B1 | * | 3/2001 | Trese et al. | 210/806 |

OTHER PUBLICATIONS

Methods of Enzymology, vol. 80, No. 29, 1981, Academic Press, Inc., pp. 365–379, Francis J. Castellino and James R. Powell, "Human Plasminogen".

* cited by examiner

Primary Examiner—John Kim
(74) Attorney, Agent, or Firm—Gifford, Krass, Groh, Sprinkle, Anderson & Citkowski, P.C.

(57) ABSTRACT

A method for rapid purification of a blood component from blood is described in which the blood plasma is first separated from the cellular blood elements by any conventional means, such as centrifugation. An affinity cartridge is then activated with a molecule, such as an amino acid, which binds with a blood component such as plasminogen. The separated blood plasma is then passed through the affinity cartridge such that the blood component is retained by the affinity cartridge. Thereafter, the blood component is eluted from the affinity cartridge by passing a buffer solution containing a releasing agent through the affinity cartridge. This releasing agent disengages the blood component from the affinity cartridge. The releasing agent is then separated from the eluted solution by passing the eluted solution through a device, such as an ion exchange, gel filter, or size exclusion device. The isolated plasminogen solution is then concentrated by a factor of from 2 to 10. The separated blood component, e.g. plasminogen, is then converted to plasmin by adding a known amount of an enzyme to the solution from which the releasing agent has been removed.

23 Claims, 3 Drawing Sheets

RAPID PROCESS FOR PURIFICATION AND CONCENTRATION OF PLASMIN

FIELD OF THE INVENTION

The present invention relates to a rapid process for purification and concentration of a blood component and, in particular, the purification and concentration of plasminogen which is then converted to plasmin for use in surgical procedures.

BACKGROUND OF THE INVENTION

With concerns about identifying ever-changing strains of HIV, hepatitis, and other blood born pathogens, the use of blood bank whole blood as a source for blood components in non-emergency surgical procedures has been disfavored. As a result, it is advantageous to draw blood from a patient, extract the needed blood component, and then reintroduce the blood component into the patient during a surgical procedure. Plasminogen is exemplary of a blood component that is separated from a patient's own blood and reintroduced into the patient.

Plasminogen is a component of the fibrolytic system and is the plasmaprotein precursor of plasmin, a serine protease. Plasmin is well known to function in fibrinolysis and fibrinogenolysis, as well as digesting factor $IX_a$, and the activation of zymogens, among its many functions. Plasmin is injected systemically for the treatment of acute thrombolytic disorders. The injection of plasmin into a human eye has been shown to induce posterior vitreous detachment, as detailed in U.S. Pat. No. 5,304,118.

While methods of isolating plasminogen are well known to the art, these methods have required considerable time and equipment that precluded plasmin extraction and isolation simultaneous with a surgical procedure. As a result, blood collection from a patient and plasmin extraction and isolation had to occur prior to patient anesthesia increasing the time and cost of the surgical procedure. Exemplary of these time consuming plasminogen purification procedures are U.S. Pat. Nos. 3,943,245; 5,371,007 and Castellino, *Methods of Enzy.*, Vol. 80, 265–337 (1981).

A rapid method for purification of plasminogen utilized an affinity cartridge under syringe pressure to selectively bind a desired blood component. The affinity cartridge was then washed with an equilibration buffer followed by injecting an elution buffer therethrough containing a release agent for the desired blood component. This method is detailed in U.S. Pat. No. 6,207,066 and is capable of delivering active plasmin from a blood sample within tens of minutes. Unfortunately, the concentration of active plasmin is lower than otherwise could be used and is often insufficient to reproducibly induce a posterior vitreous detachment. A low plasmin concentration results in decreased biological efficacy. Thus, there exists a need for a method to purify and concentrate a blood component from a whole blood sample quickly enough that the blood draw and reintroduction of the desired blood component may occur in due course of a surgical procedure.

SUMMARY OF THE INVENTION

The present invention overcomes the previously known disadvantages of the previously known blood component separation methods by providing a rapid separation and purification of a blood component utilizing the patient's own blood and which can be accomplished within a few minutes followed by concentration to provide a more potent surgical volume. The use of a concentrator eliminates the need to use large amounts of a patient's own blood or pooled plasma and reduces the volume of the plasmin injected into the eye.

Blood is first drawn from the patient and the blood plasma is separated from the cellular blood elements using conventional methods, such as centrifugation. After centrifugation, the blood plasma containing the blood component is retained and the cellular blood elements are discarded.

An affinity cartridge of the type which binds with the desired blood component is prepared prior to the time of use. L-lysine (or other protein binding component) is covalently attached to silica which has been epoxy activated. Silica is a material which can withstand very high pressure and still maintain its shape. This matrix yields low back pressure and high flow rates. One to five cubic centimeters (cc) of the lysine-silica is loaded into a cartridge and the lid is put on. The lid has a female luer-locked inlet to which a syringe can be attached. Liquids can be pushed through the cartridge with the use of a syringe at a rate which is up to ten times of that which could be achieved with the use of a gravity fed column.

A syringe containing equilibration buffer is attached to both the affinity and gel filtration cartridges and the buffer is pushed through the cartridges to pre-wet them. The syringes are discarded. A syringe containing plasma typically present from 10 cc to 25 cc is connected to the affinity cartridge. The plasma is passed through the cartridge such that the desired blood component binds with the affinity cartridge and is removed from the plasma. The plasma is then discarded.

Thereafter, an equilibration buffer is passed through the affinity cartridge to wash and remove any unbound proteins or the like that may be contained within the affinity cartridge. Upon completion of the washing step, only the bound blood component remains within the affinity cartridge.

The blood component is then eluted from the affinity cartridge by injecting an elution buffer containing a releasing agent. The releasing agent is selected such that the releasing agent frees or unbinds the blood component from the affinity cartridge. If desired, the releasing component (E-ACA) can be removed from the blood component by attaching an ion exchanging solid-phase extraction or gel filtration device to the outlet "out" of the affinity cartridge, prior to the blood component elution step. These devices consist of female luer inlets and male luer outlets. They contain strong supports which will not collapse when passing materials through them with an attached syringe. They do have limited capacity and could not be used for large scale separation purposes.

Concentrating of the blood component then occurs. The blood component concentration is raised by a factor of at least two.

A known amount of an enzyme is then added to the eluted blood component to obtain the desired subcomponent, such as plasmin. The blood component or subcomponent is then used, optionally after further filtering, as desired in the surgical procedure.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

The present invention will be described with respect to separating the blood component plasminogen from blood. The plasminogen is subsequently converted into plasmin and used for surgical procedures, such as a vitrectomy. It will be understood, of course, that other blood components may alternatively be separated from the blood utilizing the method of the present invention. These other blood components illustratively include fibrin, apolipoprotein, and antibodies.

Figure 1:
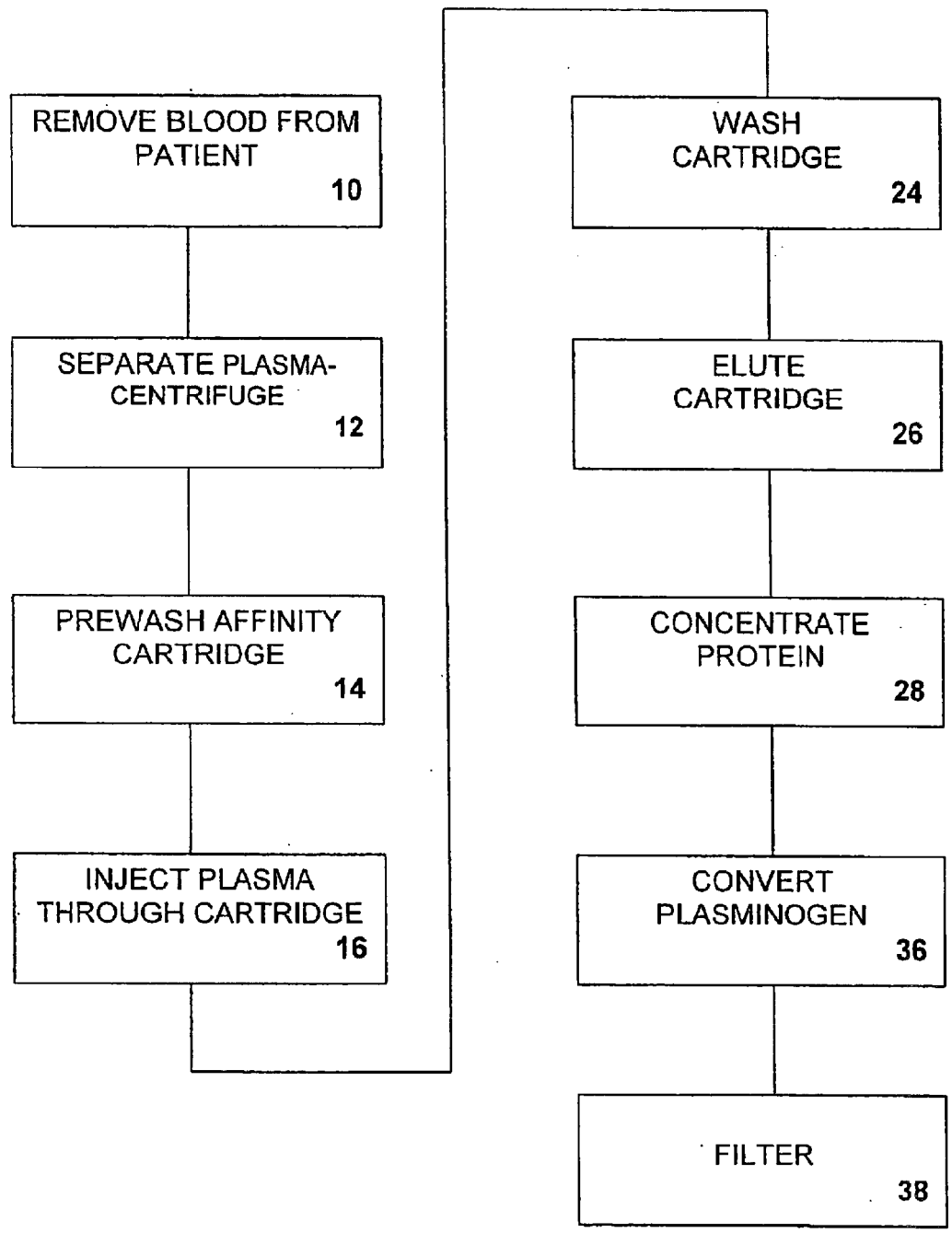
FIG. 1 is a process diagram illustrating the steps of the method of the preferred embodiment of the present invention.

With reference then to FIG. 1, at step 10 a predetermined amount of blood, for example 40 cc, is first removed from the patient in any conventional fashion such as by syringe containing an anticoagulant. The amount of blood removed from the patient will vary, of course, depending upon the final amount of the blood component required for the medical procedure.

At step 12, the blood plasma is separated from the cellular blood elements in any conventional fashion, such as by centrifuging. In the preferred embodiment of the invention, the blood is centrifuged at 1000 g for ten minutes at 25° C. The plasma is then collected in sterile syringes. Typically, 10 to 30 cc of plasma is collected. For a vitrectomy, preferably 20 to 25 cc of plasma is collected.

Figure 2:
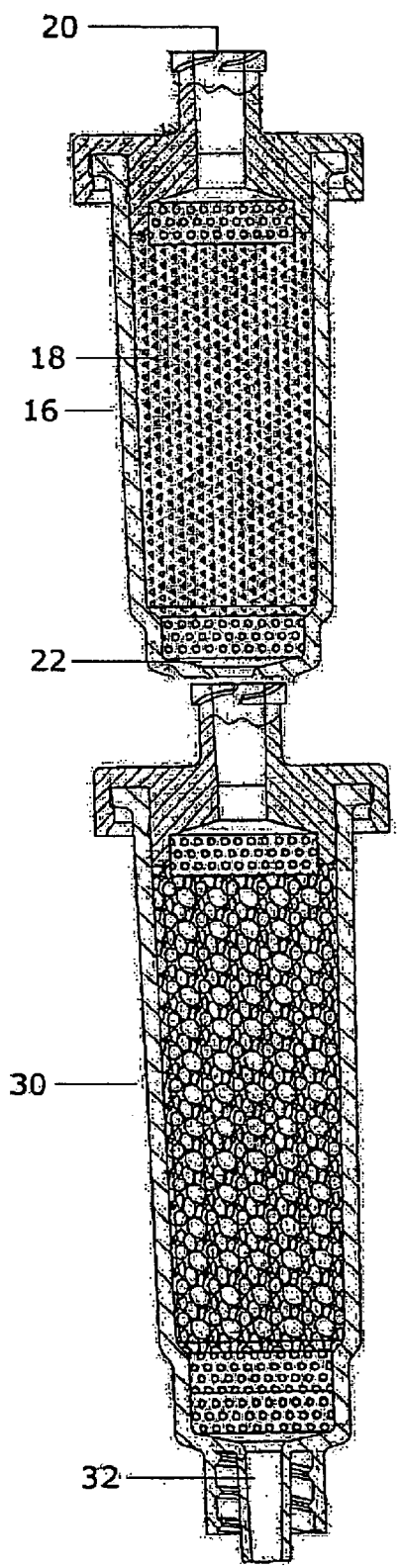
FIG. 2 is a side view of an affinity cartridge coupled with a gel filtration cartridge.

With reference now to FIGS. 1 and 2, at step 14 (FIG. 1), an affinity cartridge 16 (FIG. 2) is pre-washed with an equilibration buffer solution. The affinity cartridge 16 includes a solid support 18 having an amino acid, such as L-lysine, affixed to it. The affinity cartridge also includes a luer inlet 20 and an outlet 22 such that all liquid injected into the inlet 20 passes through the solid support 18 and out through the outlet 22. After pre-washing the affinity cartridge 16 with the equilibration buffer, the equilibration buffer is discarded.

The affinity cartridge 16 can typically contain 1 to 5 cc packed volume of affinity medium such as L-lysine bound to a rigid support such as epoxy-activated silica beads. Preferably, 2 to 4 cc of affinity medium is utilized herein. Other alternative beads can include a ceramic matrix illustratively including alumina or titania with lysine attached via an epoxy-activated linkage. The affinity media must be capable of withstanding the application of pressure necessary for performing rapid elution throughput without collapsing on itself. The pressure operative herein is defined to be at least the pressure exerted by forcing a syringe plunger manually downward against the back pressure induced by the affinity cartridge. Pressures generated herein are typically 1.5 to 10 atmospheres. The epoxy-activated silica beads operative herein are manufactured by Waters Corporation. Such beads typically have a diameter of 40 $\mu$m, a pore size of 50 nm and a binding capacity of 3–7 $\mu$moles of lysine per (ml) of packing material.

The lysine (L-lysine monohydrochloride, Sigma Chemical (L-6027) is then bound to the silica by conventional methods. The silica is then packed into a cartridge typically made of polypropylene with polyethylene frits. It has a luer lock fitting for syringe attachment and is capable of tolerating syringe pressures and conventional sterilization processing.

An equilibration buffer containing primarily potassium phosphate can be used to pre-wash the affinity cartridge 16. Approximately 10 cc or more of the equilibration buffer are passed through the affinity cartridge 16 during the pre-wash step 14.

At step 16 the plasma separated at step 12 is injected into the inlet 20 of the affinity cartridge 16 so that the plasma passes through the solid support 18 and out through the cartridge outlet 22. In doing so, the blood component plasminogen reacts with the amino acid L-lysine and the plasminogen binds to the amino acid on the solid support 18 in the affinity cartridge. The plasma with the plasminogen removed is collected from the outlet port 22 of the cartridge 16 is then discarded.

At step 24 the cartridge containing the bound plasminogen is then washed to remove any unbound protein contained within the cartridge 16. Such washing is accomplished by passing approximately 60 cc of an equilibration buffer through the cartridge 16. The buffer is injected through the cartridge 16 and is then discarded. In doing so, only the bound plasminogen remains attached to the affinity cartridge 16.

A gel filtration, ion exchange, or size exclusion device 30 is coupled in series, e.g. with a luer coupling, with the outlet port 22 from the affinity cartridge so that all solution passing through the cartridge 16 also passes through the gel filtration, ion exchange or size exclusion filter 30. In a preferred embodiment the filter 30 is a gel filtration filter. An exemplary gel filtration medium is G-25 fine Sephadex (Amersham Biosciences). It is appreciated that other gel media are operative to filter the desired blood plasma component. A gel filtration medium is illustratively pre-washed by passing 10 cc of 100 milimolar potassium phosphate buffer therethrough. A Maxi-Clean disk (Alltech Associates, Inc.) can include, for example, a solid-phase extraction device which consists of high purity polystyrene-divinylbenzene cation exchange resin beads sandwiched between polyethylene frits 40 housed in a medical-grade polypropylene housing. At step 26 (FIG. 1) the plasminogen is then eluted from the affinity cartridge 16 by injecting 2 to 4 cc solution of elution buffer containing a releasing agent, such as $\epsilon$-amino-n-caproic acid. The releasing agent effectively releases the bound plasminogen from the affinity cartridge 16 so that the solution from the affinity cartridge contains elution buffer, the releasing agent and the blood component plasminogen.

The gel filtration or ion exchange device 30 is coupled in series with the affinity cartridge 16. The eluted solution of the elution buffer, releasing agent and plasminogen passes through the gel filtration or ion exchange device 30. The device 30 binds with, or retards the releasing agent and effectively removes the releasing agent from the solution. Consequently, the filtered solution passing through the outlet port 32 of the device 30 contains only an acceptable amount of the elution buffer and the eluted plasminogen.

Figure 3:
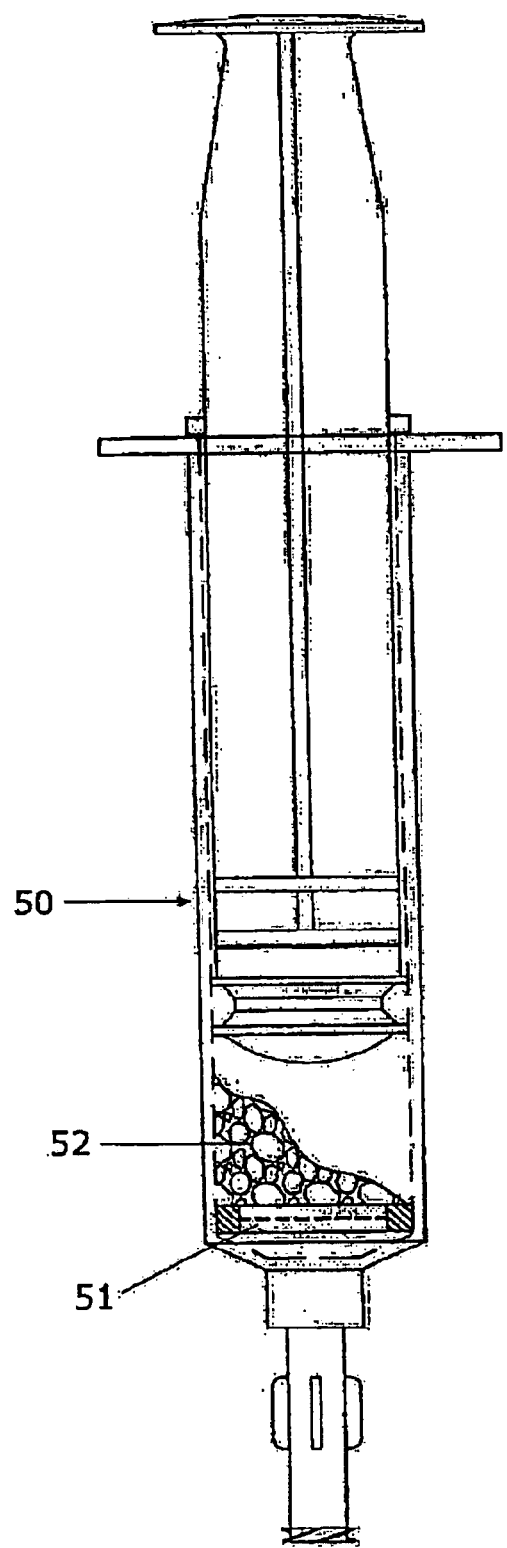
FIG. 3 is a partial cutaway side view of an inventive blood component concentrator syringe.

The elution buffer and eluted plasminogen are then loaded into a syringe with a nylon frit 51 in a polypropylene housing shown generally at 50 in FIG. 3 containing a preselected dry quantity of a Sephadex G-50 or similar material 52. The dry quantity absorbs a known quantity of solvent thereby concentrating the plasminogen step 28 in the remaining solvent. The plasminogen is concentrated by a factor of at least two. Preferably, plasminogen is concentrated by a factor of between 3 and 10. For example, 2.8 cc of eluted buffer and plasminogen yields 0.7 ml upon contacting 0.34 grams of G-50 Sephadex thereby increasing plasminogen concentration to a final concentration of 1.5–3.0 milligrams per milliliter. The concentrating of plasminogen preferably relies on the ability of an immobilized substance such as a Sephadex or the above recited filtration medium to absorb a well-defined quantity of a solution without absorbing the plasminogen. It is appreciated that the inventive concentration of a purified blood component such as plasminogen alternately occurs by: ultracentrifugation through a dialysis membrane, having a molecular weight cutoff sufficient to exclude the passage of plasminogen; freeze drying; or layering the plasminogen solution onto a high osmalality solution, such as 20% by weight aqueous sucrose in order to draw solvent away from the layered plasminogen solution.

As used herein, a unit is defined in terms of activity per milliliter based upon the difference between initial and final optical absorbance multiplied by a constant for the cleavage of a synthetic substrate (D-val-leu-lys-pnitroanilide dihydrochloride) measured at a wavelength of 405 nanometers. Absorption studies, for example, are performed by adding 950 μl of lysine buffer and 250 μl of substrate to a cuvette and zeroing the initial absorbance. 50 μl of plasmin is then added and the absorbance one minute later is measured as the final absorbance.

This concentrated solution is collected in a sterile tube (not shown) which may contain a known amount of enzyme, such as streptokinase. The enzyme effectively converts the plasminogen to plasmin at room temperature 36. Optionally, pH is adjusted prior to conversion by addition of a known volume of a pH modifying agent, such as sodium hydroxide.

Optionally, at step 38, the plasmin is sterilized by passing the plasmin through a filter, such as a 0.22 micron filter such as a Corning 21032-13 assembly containing a cellulose acetate membrane in a polypropylene housing, prior to use. It is appreciated that a sterilization filter is optionally incorporated into one of the aforementioned components, preferably the final concentrator syringe. If any delay is required before the plasmin is to be used, it should be stored at lower temperatures until required.

The above-described separation of the blood component plasminogen and its subsequent conversion into plasmin can be accomplished in the matter of a few minutes in the operating room or laboratory. The present invention can also include a kit for rapid purification of plasmin from human plasma. The kit can include a syringe, a lysine affinity cartridge, a gel filtration cartridge, a filter adapted to be attached to a syringe (i.e., 0.22 μm), a syringe concentrator, and suitable buffers and reagents necessary for separating, purifying and concentrating plasmin.

EXAMPLE

A kit designed for the rapid purification and activation of autologous plasmin was utilized. Blood is drawn into 6 yellow capped (ACD) tubes which can be supplied as part of the kit. The tubes containing the blood are centrifuged at 750×g for fifteen minutes to obtain plasma separation. A sterile 21 ga needle with a check valve can be attached to a 30 cc syringe (Syringe A), the needle inserted through the cap of the blood collection tube and the plasma aspirated. This step can be repeated for the other tubes until 22 cc of plasma are collected in Syringe A. All syringes are sterile medical grade syringes.

The gel filtration cartridge and affinity cartridges are pre-wetted by attaching a 10 cc syringe containing sterile 100 mM K phosphate buffer, pH 7.5, and injecting it through the cartridges. The buffer is then discarded and the gel filtration device can be set aside until the elution step.

The affinity cartridge is then attached to the end of syringe A and the plasma is then injected slowly through the cartridge to allow the plasminogen to bind to the cartridge. The syringe may then be discarded.

The affinity cartridge is then attached to a 60 cc syringe (Syringe B) containing 60 cc of sterile 100 mM K phosphate, pH 7.5. The buffer is injected through the cartridge to remove any unbound material from the affinity cartridge. For optimum recovery it is essential to wait until dripping from the end of the cartridge has completely ceased before proceeding to the next step. The syringe is then removed and discharged.

The affinity cartridge is then attached to a 10 cc syringe (Syringe C) containing 4 cc of sterile 19 mM ε-amino caproic acid (AMICAR, American Reagent Laboratories) in 100 mM K phosphate, pH 7.5. The gel filtration cartridge is then attached to the end of the affinity cartridge. The contents of Syringe C are then injected through the cartridges and discarded.

The assembled unit is then attached to the end of Syringe D. The contents of Syringe D (2.6 cc of sterile 100 mM K phosphate, pH 7.5 and 19 mM ε-amino caproic acid (AMICAR, American Reagent Laboratories) is then injected through the assembly into an empty 10 cc syringe. The empty 10 cc syringe is attached to the assembly with a female/female luer lock adapter. The syringe and adaptor are detached from the assembly. The plunger in the syringe is pulled back to the 5 cc line.

The plasminogen solution is then loaded into the concentrator syringe containing 0.34 grams of Sephadex G-50 by attaching the concentrator to the adaptor on the syringe containing the plasminogen and injecting the plasminogen into the concentrator. Upon allowing one minute contact time therebetween for Sephadex water uptake, the reduced volume plasminogen solution is optionally injected through a 0.22 micron sterilization filter.

The plasminogen is then collected in a sterile vial that contains 25,000 IU of sterile streptokinase. The vial is then gently agitated and then incubated at room temperature for 10 minutes to allow for the conversion of plasminogen to plasmin to take place. The final plasmin activity is 10 to 15 units/ml.

To confirm that active plasmin is present, a drop of plasmin can be placed in a well of an indicator plate which contains a synthetic substrate (D-val-leu-lys-pNA, Sigma (V-0882)). Cleavage of the substrate produces a bright yellow color which can be compared to an enclosed standard.

The plasmin is now ready for use such as for injection into the eye.

Patents and publications mentioned in the specification are indicative of the levels of those skilled in the art to which the invention pertains. These patents and publications are incorporated herein by reference to the same extent as if each individual patent or publication was specifically and individually incorporated herein by reference.

It will, of course, be understood that different blood components utilizing different binding agents and different releasing agents may alternatively be used without deviation from the spirit or scope of the present invention. Having described our invention, many modifications thereto will become apparent to those skilled in the art to which it pertains without deviation from the spirit of the invention as defined by the scope of the appended claims.

What is claimed is:

1. An improved method for rapid purification of a plasminogen including separating blood plasma from cellular blood elements, pre-washing an affinity cartridge of the type that bind the plasminogen, retaining the plasminogen on the affinity cartridge, passing the blood plasma through the affinity cartridge, eluting the plasminogen from the affinity cartridge by passing a releasing agent through the affinity cartridge, and separating the releasing agent front the solution containing both the releasing agent and the plasminogen wherein the improvement lies in: concentrating the plasmingen by a factor of from 2 to 10 in the presence of a solvent insoluble concentrating medium that absorbs a predetermined quantity of a solvent.

2. The improved method of claim 1 wherein the solvent insoluble concentrating medium is selected from group consisting of: beaded gel of dextran cross linked with epichlorohydrin, beaded agarose, and agarose.

3. The improved method of claim 1 wherein concentration occurs within a concentration syringe.

4. The improved method of claim 3 wherein the concentration syringe contains at least 0.1 gram of the solvent insoluble concentrating medium.

5. The improved method of claim 1 wherein the concentrating medium absorbs an amount of the solvent to at least 20% by weight of the medium.

6. A method for rapid purification and concentration of plasminogen from blood comprising the steps of:

separating blood plasma from cellular blood elements without prior solvent extraction;

pre-washing an affinity cartridge of the type which binds with plasminogen, said affinity cartridge containing affinity medium selected from a group consisting of silica matrix and ceramic matrix;

passing the separated blood plasma through the affinity cartridge so that the plasminogen is retained by the affinity media, the affinity media having a solid support which can withstand high pressure and a molecule disposed thereon having affinity for the plasminogen;

thereafter eluting the plasminogen from the affinity cartridge by passing a releasing agent through the affinity cartridge, the releasing agent disengaging the plasminogen from the affinity cartridge;

thereafter separating the releasing agent from the solution containing both the eluted releasing agent and the plasminogen to yield a plasminogen solution; and concentrating the plasminogen solution by a factor of from 2 to 10 to form a concentrated solution;

wherein concentrating occurs in the presence of a solvent insoluble concentrating medium that absorbs a predetermined quantity of a solvent.

7. The method of claim 6 wherein the concentrated solution comprises 1.5–3.0 milligrams of plasminogen per milliliter.

8. The method of claim 6 wherein concentration occurs within a concentration syringe.

9. The method of claim 6 wherein the concentrating medium absorbs an amount of the solvent to at least 20% by weight of the medium.

10. The method of claim 6 further comprising the step of converting said plasminogen following said separation of the releasing agent.

11. The method of claim 10 wherein said converting step comprises the step of introducing an enzyme to the plasminogen.

12. The method of claim 11 wherein the enzyme is selected from the group consisting of: streptokinase, urokinase and tissue plasminogen activator.

13. An improved method for rapid purification of a blood component including separating blood plasma from cellular blood elements, pre-washing an affinity cartridge of the type that bind the blood component, retaining the blood component on the affinity cartridge, passing the blood plasma through the affinity cartridge, eluting the blood component from the affinity carbidge by passing a releasing agent through the affinity cartridge, and separating the releasing agent from the solution containing both the releasing agent and the blood component wherein the improvement lies in: concentrating the blood component by a factor of from 2 to 10, wherein concentrating occurs in the presence of a solvent insoluble concentrating medium that absorbs a predetermined quantity of a solvent.

14. The improved method of claim 13 wherein the solvent insoluble concentrating medium is selected from the group consisting of: beaded gel of dextran cross linked with epichlorohydrin, beaded agarose, and agarose.

15. The improved method of claim 13 wherein concentration occurs within a concentration syringe.

16. The improved method claim 15 wherein the concentration syringe contains at least 0.1 gram of the solvent insoluble concentrating medium.

17. The improved method of claim 13 wherein the concentrating medium absorbs an amount of the solvent to at least 20% by weight of the medium.

18. A method for rapid purification and concentration of plasminogen from blood comprising the steps of:

separating blood plasma from cellular blood elements without prior solvent extraction;

pre-washing an affinity cartridge of the type which binds with plasminogen, said affinity cartridge containing affinity medium selected from a group consisting of silica matrix and ceramic matrix;

passing the separated blood plasma through the affinity cartridge so that the plasminogen is retained by the affinity media, the affinity media having a solid support which can withstand high pressure and a molecule disposed thereon having affinity for the plasminogen;

thereafter eluting the plasminogen from the affinity cartridge by passing a releasing agent through the affinity cartridge, the releasing agent disengaging the plasminogen from the affinity cartridge;

thereafter separating the releasing agent from the solution containing both the eluted releasing agent and the plasminogen to yield a plasminogen solution; and concentrating the plasminogen solution by a factor of from 2 to 10 to form a concentrated solution, wherein concentrating occurs in the presence of a solvent insoluble concentrating medium that absorbs a predetermined quantity of a solvent;

wherein the concentrated solution comprises 1.5–3.0 milligrams of plasminogen per milliliter.

19. The method of claim 18 wherein concentration occurs within a concentration syringe.

20. The method of claim 18 wherein the concentrating medium absorbs an amount of the solvent to at least 20% by weight of the medium.

21. The method of claim 18 further comprising the step of converting said plasminogen following said separation of the releasing agent.

22. The method of claim 21 wherein said converting step comprises the step of introducing an enzyme to the plasminogen.

23. The method of claim 22 wherein the enzyme is selected from the group consisting of: streptokinase, urokinase and tissue plasminogen activator.

* * * * *

UNITED STATES PATENT AND TRADEMARK OFFICE
CERTIFICATE OF CORRECTION

PATENT NO. : 6,855,263 B2
DATED : February 15, 2005
INVENTOR(S) : Michael Trese et al.

It is certified that error appears in the above-identified patent and that said Letters Patent is hereby corrected as shown below:

<u>Column 7,</u>
Line 5, "front" should be changed to -- from --.

Signed and Sealed this

Twelfth Day of July, 2005

JON W. DUDAS
*Director of the United States Patent and Trademark Office*